United States Patent
Cecchi et al.

(10) Patent No.: US 10,665,330 B2
(45) Date of Patent: May 26, 2020

(54) CORRELATING OLFACTORY PERCEPTION WITH MOLECULAR STRUCTURE

(71) Applicant: INTERNATIONAL BUSINESS MACHINES CORPORATION, Armonk, NY (US)

(72) Inventors: Guillermo A. Cecchi, New York, NY (US); Amit Dhurandhar, Yorktown Heights, NY (US); Pablo Meyer rojas, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 848 days.

(21) Appl. No.: 15/296,597

(22) Filed: Oct. 18, 2016

(65) Prior Publication Data

US 2018/0107803 A1    Apr. 19, 2018

(51) Int. Cl.
*G06F 17/50* (2006.01)
*G16C 20/30* (2019.01)
(Continued)

(52) U.S. Cl.
CPC .......... *G16C 20/30* (2019.02); *C12Q 1/6876* (2013.01); *G01N 33/0036* (2013.01);
(Continued)

(58) Field of Classification Search
USPC .............................. 703/5, 2, 6; 426/534, 538
See application file for complete search history.

(56) References Cited

U.S. PATENT DOCUMENTS

2005/0096852 A1* 5/2005 Turin ................. C11B 9/00
702/22
2010/0143337 A1* 6/2010 Matsunami .......... C12Q 1/6876
424/130.1
(Continued)

FOREIGN PATENT DOCUMENTS

WO    2013035070 A1    3/2013

OTHER PUBLICATIONS

Guillermo Cecchi, "Prediction of Olfactory and Taste Perception Through Semantic Encoding", Related Application, U.S. Appl. No. 15/819,710, filed Nov. 21, 2017.
(Continued)

*Primary Examiner* — Thai Q Phan
(74) *Attorney, Agent, or Firm* — Cantor Colburn LLP; Vazken Alexanian (57) ABSTRACT

Predicting human olfactory perception based on molecular structure is described. Molecular descriptor data indicative of molecular descriptors associated with a group of molecular samples can be obtained. Olfactory perception indicator (OPI) data for a set of OPIs can also be obtained with respect to the molecular samples. A training model can be executed on the molecular descriptor data and the OPI data to yield an output model that correlates molecular attributes with OPIs for a single individual or across an aggregate of individuals. The output model can be used to predict olfactory perception for a particular compound or mixture based on which OPIs are correlated with molecular descriptors of the compound or mixture in the output model. The output model can also be inverted and used to identify molecular descriptors that are correlated with a desired set of OPIs. A molecular construct having the molecular descriptors can then be generated.

20 Claims, 5 Drawing Sheets

(51) Int. Cl.
  *G16C 20/70* (2019.01)
  *C12Q 1/6876* (2018.01)
  *G01N 33/00* (2006.01)
(52) U.S. Cl.
  CPC . *G01N 33/0073* (2013.01); *G01N 2201/1293* (2013.01); *G16C 20/70* (2019.02)

(56) References Cited

U.S. PATENT DOCUMENTS

| | | | | |
|---|---|---|---|---|
| 2010/0248390 | A1* | 9/2010 | Matsunami | G01N 33/566 436/501 |
| 2012/0015841 | A1* | 1/2012 | Shekdar | G01N 33/502 506/9 |
| 2012/0143804 | A1 | 6/2012 | Haddad et al. | |
| 2013/0236417 | A1* | 9/2013 | Ray | A01N 61/00 424/84 |
| 2013/0280400 | A1* | 10/2013 | Bartoshuk | A23L 27/39 426/538 |
| 2015/0223458 | A1* | 8/2015 | Ray | A01N 61/00 424/84 |
| 2015/0235136 | A1* | 8/2015 | Dillon | G06N 5/04 706/46 |
| 2016/0091419 | A1 | 3/2016 | Watson et al. | |
| 2018/0089739 | A1* | 3/2018 | Cecchi | G06Q 30/0631 |
| 2019/0171673 | A1* | 6/2019 | Sobel | A61B 5/4011 |
| 2019/0254322 | A1* | 8/2019 | Bartoshuk | A23L 19/00 |

OTHER PUBLICATIONS

List of IBM Patents or Patent Applications Treated As Related; (Appendix P), Filed Nov. 21, 2017; pp. 1-2.
Edwards et al., "Correlation of odor intensities with structural properties of odorants." Chemical Senses 14.2 (1989): 281-291.
Kerman et al., "Molecular complexity determines the number of olfactory notes and the pleasantness of smells." Scientific reports 1 (2011): 206.
Lawless et al., "Consistency of multidimensional scaling models derived from odor sorting." Journal of Sensory Studies 5.4 (1990): 217-230.
Mateo, "Recognition systems and biological organization: the perception component of social recognition." Annales Zoologici Fennici. Finnish Zoological and Botanical Publishing Board, 2004.
Zarzo, "Hedonic judgments of chemical compounds are correlated with molecular size." Sensors 11.4 (2011): 3667-3686. http://www.mdpi.com/1424-8220/11/4/3667/htm.

* cited by examiner

CORRELATING OLFACTORY PERCEPTION WITH MOLECULAR STRUCTURE

BACKGROUND

The present invention relates generally to predicting user perception of stimuli, and more specifically, to predicting user olfactory perception of stimuli based on molecular structure. The present invention also relates to constructing molecular compositions having desired olfactory characteristics.

Molecular compounds and mixtures of molecular compounds can exhibit various olfactory characteristics that elicit a variety of human responses. For example, a particular compound or mixture can exhibit a flowery scent that most individuals would find pleasing. In the alternative, another compound or mixture can have an odor that most people would find distasteful. Further, in certain scenarios, a compound or mixture can exhibit olfactory characteristics that elicit a spectrum of responses.

SUMMARY

In one or more example embodiments of the invention, a method for correlating molecular structure with olfactory perception is described. The method includes obtaining olfactory perception indicator (OPI) data for a group of molecular samples, where the OPI data includes values of a set of OPIs for each of the molecular samples, and obtaining molecular descriptor data associated with the group of molecular samples. The method further includes executing one or more training models on input data that includes the OPI data and the molecular descriptor data to obtain an output model. The output model specifies correlations between a set of molecular descriptors described by the molecular descriptor data and the set of OPIs. The method additionally includes determining a subset of the set of molecular descriptors that is associated with a particular chemical compound or mixture, and determining, using the output model, a subset of the set of OPIs that is correlated with the subset of the set of molecular descriptors.

In one or more other example embodiments of the invention, a system for correlating molecular structure with olfactory perception is described. The system includes at least one memory storing computer-executable instructions and at least one processor configured to access the at least one memory and execute the computer-executable instructions to perform a set of operations. The operations include obtaining olfactory perception indicator (OPI) data for a group of molecular samples, where the OPI data includes values of a set of OPIs for each of the molecular samples, and obtaining molecular descriptor data associated with the group of molecular samples. The operations further include executing one or more training models on input data that includes the OPI data and the molecular descriptor data to obtain an output model. The output model specifies correlations between a set of molecular descriptors described by the molecular descriptor data and the set of OPIs. The operations additionally include determining a subset of the set of molecular descriptors that is associated with a particular chemical compound or mixture, and determining, using the output model, a subset of the set of OPIs that is correlated with the subset of the set of molecular descriptors.

In one or more other example embodiments of the invention, a computer program product for correlating molecular structure with olfactory perception is described. The computer program product includes a non-transitory storage medium readable by a processing circuit, where the storage medium stores instructions executable by the processing circuit to cause a method to be performed. The method includes obtaining olfactory perception indicator (OPI) data for a group of molecular samples, where the OPI data includes values of a set of OPIs for each of the molecular samples, and obtaining molecular descriptor data associated with the group of molecular samples. The method further includes executing one or more training models on input data that includes the OPI data and the molecular descriptor data to obtain an output model. The output model specifies correlations between a set of molecular descriptors described by the molecular descriptor data and the set of OPIs. The method additionally includes determining a subset of the set of molecular descriptors that is associated with a particular chemical compound or mixture, and determining, using the output model, a subset of the set of OPIs that is correlated with the subset of the set of molecular descriptors.

BRIEF DESCRIPTION OF THE DRAWINGS

The detailed description is set forth with reference to the accompanying drawings. The drawings are provided for purposes of illustration only and merely depict example embodiments of the invention. The drawings are provided to facilitate understanding of embodiments of the invention and shall not be deemed to limit the breadth, scope, or applicability of embodiments of the invention. In the drawings, the left-most digit(s) of a reference numeral identifies the drawing in which the reference numeral first appears. The use of the same reference numerals indicates similar, but not necessarily the same or identical components. However, different reference numerals can be used to identify similar components as well. Various embodiments can utilize elements or components other than those illustrated in the drawings, and some elements and/or components can be absent in various embodiments. The use of singular terminology to describe a component or element can, depending on the context, encompass a plural number of such components or elements and vice versa.

DETAILED DESCRIPTION

Example embodiments of the invention include, among other things, systems, methods, computer-readable media, techniques, and methodologies for predicting human olfactory perception based on molecular structure. Olfactory perception, as that term is used herein, includes taste sensations, sensations of smell, or the like. Any molecule's chemical structure can be fully described by at least a subset of a set of molecular descriptors. In accordance with example embodiments of the invention, molecular descriptor data indicative of molecular descriptors associated with a group of molecular samples can be obtained. Olfactory perception indicator (OPI) data that is indicative of values associated with a set of OPIs with respect to the molecular samples can then be obtained. An OPI can be any indicator of a taste sensation or a sensation of smell. An OPI that is a taste prediction indicator (TPI) can be any descriptor of a taste sensation such as, for example, sour, sweet, spicy, tangy, etc. An OPI that is a smell prediction indicator (SPI) can be any descriptor of a sensation of smell including, but not limited to, flowery, pungent, fruity, etc. The molecular descriptor data and the OPI data can be provided as input data to one or more training models. Executing the training model(s) on the input data yields a linear output model that correlates molecular attributes with OPIs for a single individual or across an aggregate of individuals. The output model can be represented as a matrix of correlations between the molecular descriptors and the OPIs.

The output model can be utilized in a variety of ways. For example, the output model can be used to predict olfactory perception for a chemical compound or mixture. In particular, molecular descriptors associated with the chemical compound or mixture can be determined and corresponding correlations to various OPIs can be determined from the output model. In this manner, the output model can be used to predict which OPIs an individual or a group of individuals can associate with a chemical compound or mixture in the absence of direct user feedback by determining which OPIs are correlated with compounds or mixtures having similar molecular descriptors. The compound or mixture can then be targeted to those individual(s) who have indicated a desire or preference for the OPIs determined to be correlated with the molecular descriptors of the compound or mixture. In certain example embodiments, only those OPIs determined to be most strongly positively correlated with the molecular descriptors of the chemical compound or mixture can be considered. For example, only those OPIs with correlation values in the output model that satisfy a threshold value (e.g., a correlation threshold) with respect to molecular descriptors of the compound or mixture can be considered.

Example embodiments of the invention are also directed to, among other things, systems, methods, computer-readable media, techniques, and methodologies for determining and generating a molecular construct that has desired olfactory attributes or characteristics. A set of desired OPIs can be determined. The output model can then be inverted to obtain an inverted output model to allow for molecular descriptors to be identified OPIs. Using the inverted output model, a set of molecular descriptors correlated (e.g., positively correlated) with the set of desired OPIs can be determined. Then, if feasible, a molecular construct having the molecular descriptors as attributes can be constructed. In certain example embodiments, a consumer product containing the molecular construct can be produced and targeted to individuals associated with the desired set of OPIs.

Example embodiments of the invention provide a number of benefits over conventional approaches and such benefits can be realized across a wide range of industries. Conventional approaches recognize that a molecular compound or mixture can have certain olfactory attributes that are determined by aspects of its molecular structure. For example, a certain chemical structure (e.g., a specific arrangement of elements and chemical bonds between the elements) can have a known olfactory attribute (e.g., flowery scent). More specifically, olfactory receptors in a human nose or on a human tongue, for example, can bind a molecule having a certain chemical structure, which can stimulate a signal in the brain that causes a particular olfactory characteristic to be detected. Such conventional approaches, however, are incapable of predicting individual olfactory perception or mean olfactory perception across a group of individuals based on correlations between OPIs and molecular descriptors.

Example embodiments of the invention can provide manufacturers or other interested entities with valuable information regarding an association between an object's olfactory characteristics and predicted human responses to those characteristics, thereby allowing these entities to engage in more targeted olfactory branding. For example, manufacturers can utilize example embodiments of the invention to enhance the marketing appeal of their products based on odors they emanate. As another example, manufacturers can extend the predictive capabilities of example embodiments of the invention to develop new products having molecular attributes correlated with olfactory characteristics that are customized to particular users or user groups.

Other potential benefits of example embodiments of the invention include providing analytics to manufacturers or other industry participants to improve the sales and development of its offerings; identifying local, cultural, genetic, and temporal trends based on aggregate predictions across a group of individuals to aid in product design, marketing, and olfactory branding; targeting industries or specific products to particular consumers; bridging expert ontology for describing olfactory characteristics of a product with consumer ontology; generating lists of compounds required to produce a desired aroma accurately and cost effectively; scent marketing/olfactory branding; and so forth.

Example embodiments of the invention can also be used to enhance a wide range of disciplines involving human olfactory responses. For example, in the field of appetite management, odors have been shown to affect appetite and can be used in weight control as well as appetite management in chemotherapy patients. Example embodiments of the invention can provide an understanding of the scents/odors associated with increased and decreased food consumption, which can make it possible for food manufacturers, food purveyors, dietary organizations, or the like to more effectively manage human appetite. As another example, example embodiments of the invention have applicability in the field of odor cancellation. For example, the predictive capabilities of example embodiments can be used to determine which compounds when combined together would result in neutral scents. Such an application could aid in making environments or products with unpleasant odors more appealing or engaging (e.g., public restrooms). Example embodiments also have applicability in the field of lossy compression, where they can be used to determine, from a set of compounds having a known scent, a subset of compounds or different compounds that produce the same aroma more simply or cost-effectively.

In addition, example embodiments have applicability in the field of virtual reality (VR). Conventional VR uses auditory and visual cues, but not olfactory cues. The ability to generate odor within a VR based on environmental cues could be provided based on example embodiments of the invention. Further, the field of affective computing (computing based on user emotion) currently uses data from wearable devices, but does not incorporate olfactory perception data. Example embodiments of the invention can provide olfactory perception data that can improve affective computing capabilities. In addition, example embodiments of the invention can be used to increase overall human health because the sense of smell, for example, has been linked to mortality and morbidity. For example, correlations between sense of smell and genetics could be used as a cost-effective screen to identify potential matches for organ or bone marrow transplants. It should be appreciated that the above examples of potential areas of applicability of example embodiments of the invention are merely illustrative and not exhaustive.

Figure 1:
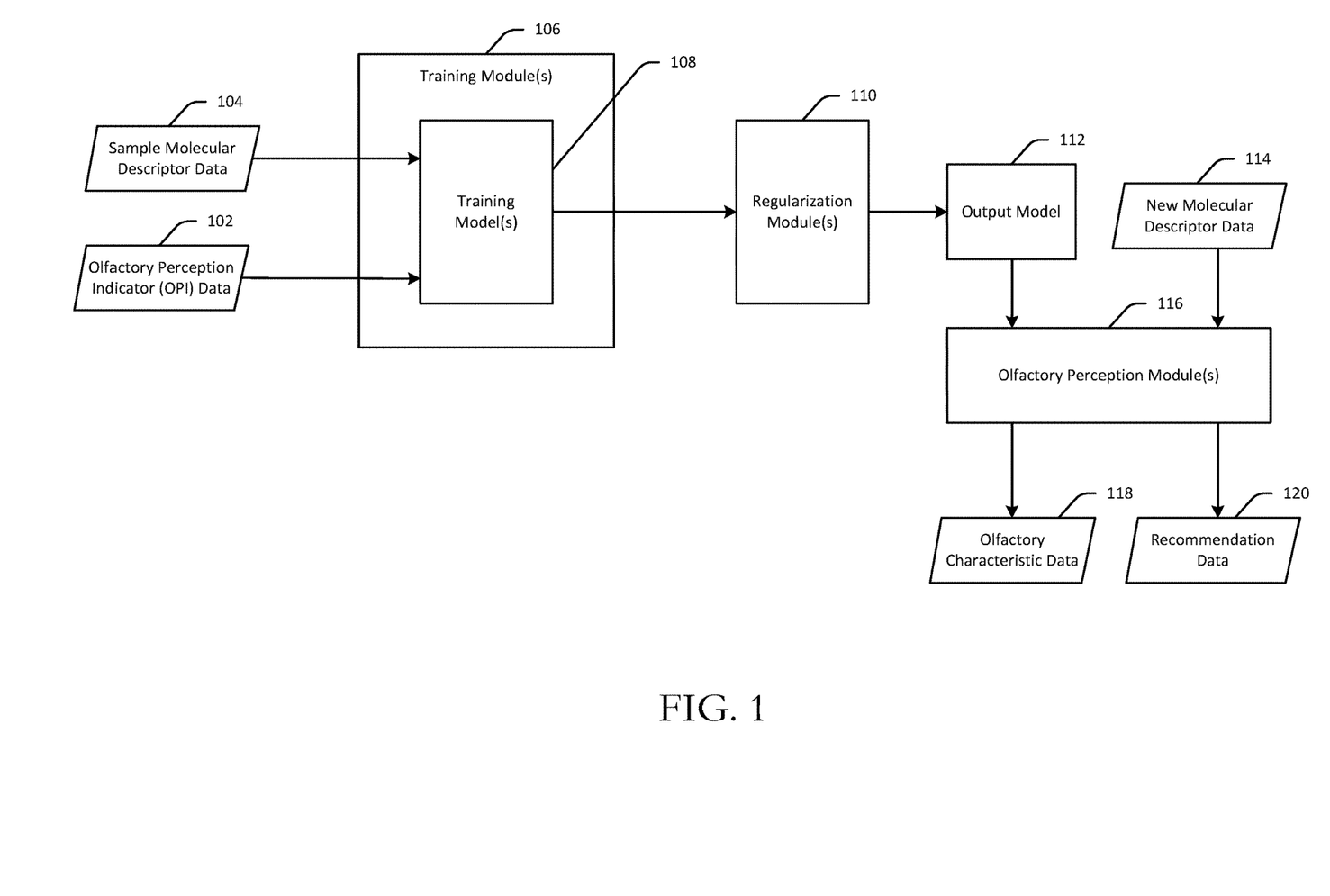
FIG. 1 is a data flow and block diagram schematically depicting the generation of an output model for predicting olfactory perception based on molecular structure in accordance with one or more example embodiments of the invention.
Figure 2:
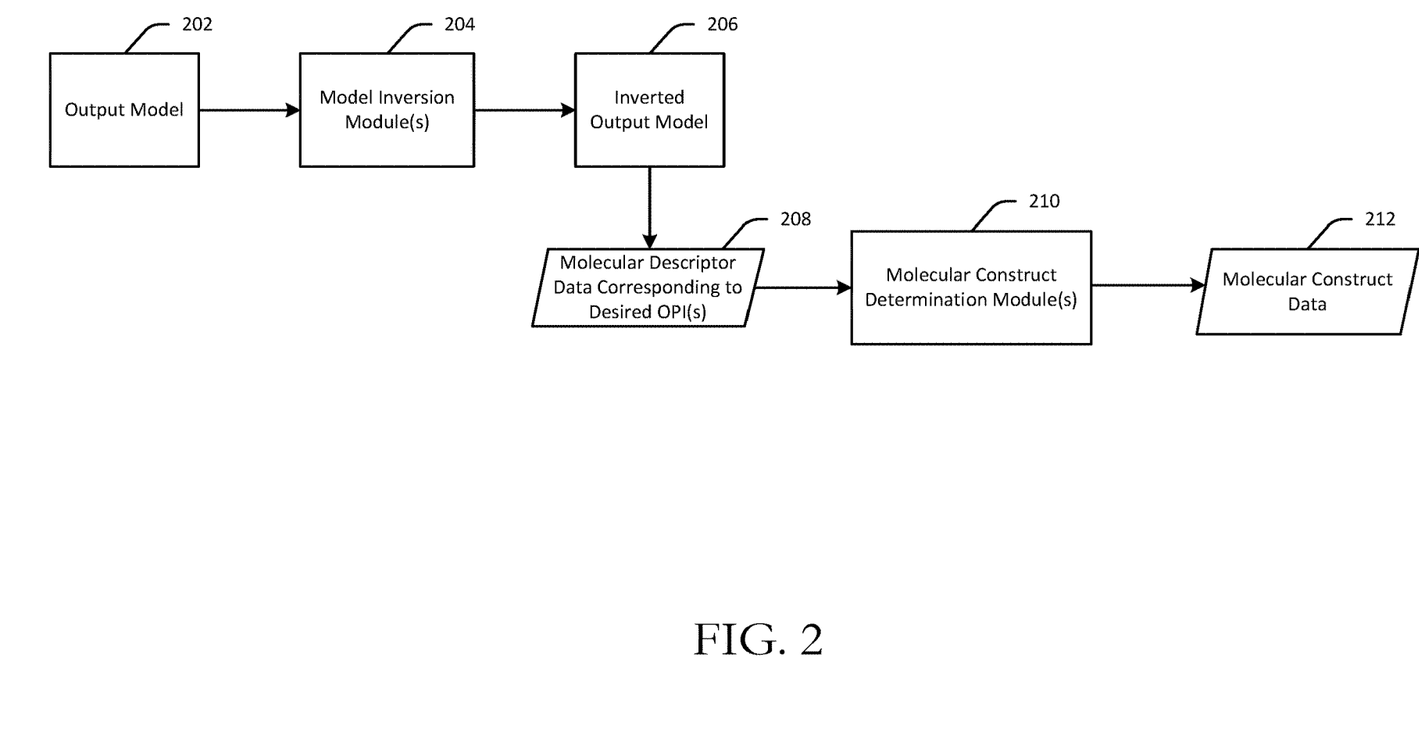
FIG. 2 is a data flow and block diagram schematically depicting the generation of a molecular construct having desired olfactory characteristics in accordance with one or more example embodiments of the invention.
Figure 3:
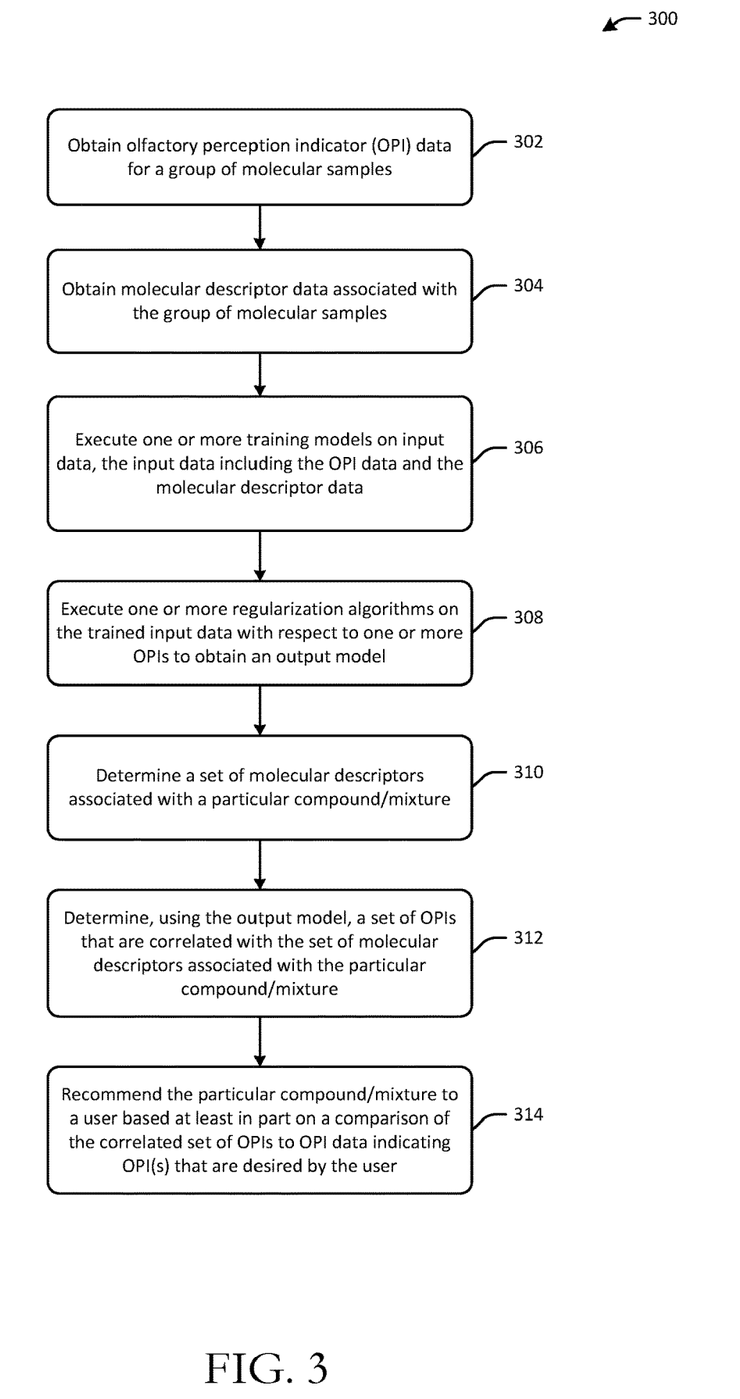
FIG. 3 is a process flow diagram of an illustrative method for generating an output model for predicting olfactory perception based on molecular structure in accordance with one or more example embodiments of the invention.
Figure 4:
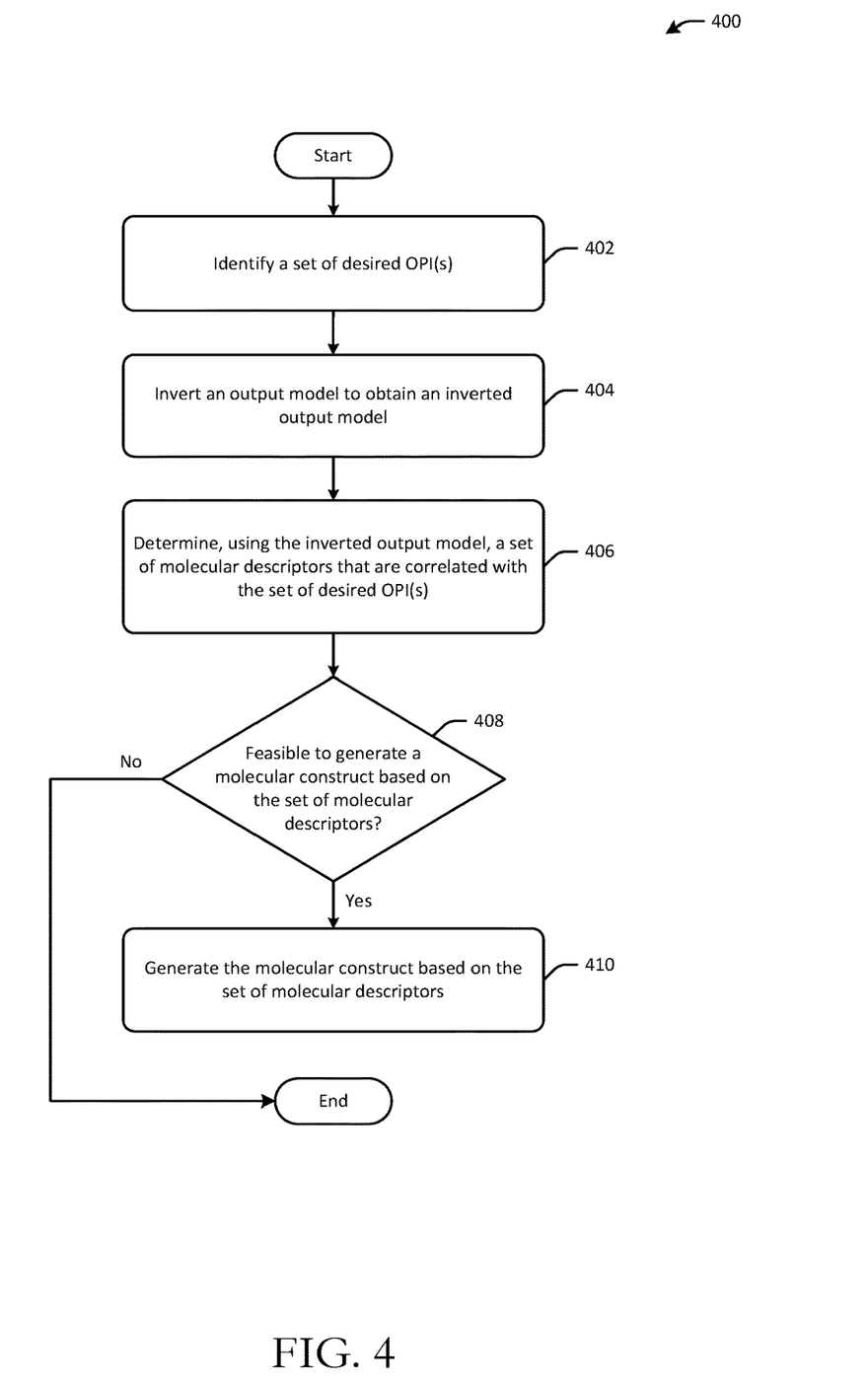
FIG. 4 is a process flow diagram of an illustrative method for generating a molecular construct having desired olfactory characteristics in accordance with one or more example embodiments of the invention.

Turning now to a more detailed description of aspects of the present invention, FIG. 1 is a data flow and block diagram schematically depicting the generation of an output model for predicting olfactory perception based on molecular structure in accordance with one or more example embodiments of the invention. FIG. 2 is a data flow and block diagram schematically depicting the generation of a molecular construct having desired olfactory characteristics in accordance with one or more example embodiments of the invention. FIG. 3 is a process flow diagram of an illustrative method 300 for generating an output model for predicting olfactory perception based on molecular structure in accordance with one or more example embodiments of the invention. FIG. 4 is a process flow diagram of an illustrative method 400 for generating a molecular construct having desired olfactory characteristics in accordance with one or more example embodiments of the invention. FIGS. 1 and 3 and FIGS. 2 and 4 will be described in conjunction with one another hereinafter.

Each operation of the method 300 and/or the method 400 can be performed by one or more program modules depicted in FIGS. 1-2. These program modules can be implemented in any combination of software, firmware, and/or hardware. One or more of these program modules can be executable across one or more olfactory prediction servers having the illustrative configuration depicted in FIG. 5, which will be described later in this description. The program modules can include computer-executable instructions that when executed by a processing circuit cause one or more operations to be performed. A system or device described herein as being configured to implement example embodiments of the invention can include one or more processing circuits, each of which can include one or more processing units or nodes. Computer-executable instructions can include computer-executable program code that when executed by a processing unit can cause input data contained in or referenced by the computer-executable program code to be accessed and processed to yield output data.

Referring first to FIG. 1 in conjunction with FIG. 3, at block 302, OPI data 102 for a group of molecular samples can be obtained. The OPI data 102 can include values specified for a set of OPIs by one or more individuals with respect to the group of molecular samples. The group of molecular samples can include any number of molecular compounds or mixtures of compounds. In certain example embodiments, the same molecular compound or mixture in the sample can be provided in multiple dilutions to increase the sample size of the molecular structures that are analyzed. One or more individuals can evaluate the group of molecular samples by assigning a respective score for each OPI in a set of OPIs with respect to each molecular sample. The OPIs can include, without limitation, the following perception indicators: fruit, fish, garlic, spices, cold, sour, burnt, acid, warm, musky, sweaty, bakery, sweet, ruinous, decayed, wood, grass, flower, and chemical. Intensity and pleasantness can also be included as additional OPI indicators. Alternatively, intensity and pleasantness can be attributes that an individual provides a value for on a predetermined scale for each OPI. For example, an individual can rate the intensity and/or pleasantness of a molecular sample with respect to the "spicy" OPI, the "sour" OPI, and so forth.

In certain example embodiments, each molecule in the group of molecular samples can be presented to one or more individuals in different concentrations, and the individual(s) can rate different sets of OPIs with respect to the different concentrations. For example, individual(s) can be asked to rate the "high" concentration molecular samples with respect to the "pleasantness" OPI and each other OPI and rate the "low" concentration molecular samples with respect to "intensity" alone. Alternatively, all concentrations of the molecular samples can be rated with respect to each OPI. In still other example embodiments, in addition to providing ratings for each of the OPIs, individual(s) can also provide a separate "intensity" rating for each OPI that indicates the perceived intensity of that OPI. The user ratings can be based on a predetermined scale, where one end of the scale is representative of complete absence of an OPI and the other end of the scale is representative of complete presence of an OPI. In certain example embodiments, the ratings can be normalized across an aggregate number of individuals. Further, in certain example embodiments, the ratings can be aggregated across multiple individuals and a statistical measure (e.g., mean, median, etc.) can be generated to reflect aggregate olfactory perception for the group of molecular samples.

At block 304, molecular descriptor data 104 associated with the group of molecular samples can be obtained. A comprehensive set of molecular descriptors can be used to fully describe any given molecular structure. The molecular descriptor data 104 can be indicative of a respective subset of this comprehensive set of molecular descriptors that is associated with each sample in the group of molecular samples. The set of molecular descriptors can include, for example, the 4,884 molecular descriptors specified by the Dragon chemi-informatic software. The set of molecular descriptors can be divided into two main categories including experimental measurements (e.g., pH, molar refractivity, dipole moment, etc.) and theoretical molecular descriptors, which can be derived from a symbolic representation of a molecular compound and can be further classified according to different types of molecular representation.

The different types of theoretical molecular descriptors can include 0D-descriptors, 1D-descriptors, 2D-descriptors, 3D-descriptors, and 4D-descriptors. 0D-descriptors can include, for example, constitutional descriptors that describe the arrangement of elements within a molecule, the types of chemical bonds present in the molecule, etc. 1D-descriptors can further include count descriptors that indicate, for example, the number of atoms of each element present in a molecular compound. 1D-descriptors can include, for example, lists of structural fragments, fingerprints, or the like. 2D-descriptors can include, for example, graph invariants or the like. 3D-descriptors can include, for example, 3D-Molecule Representation of Structure based on Electron Diffraction (MoRSE) descriptors; Weighted Holistic Invariant Molecular (WHIM) descriptors; Geometry, Topology, and Atom Weights Assembly (GETAWAY) descriptors; quantum-chemical descriptors; size, steric, surface, and volume descriptors; or the like. 4D-descriptors can include, for example, Grid-Independent descriptors (GRIND) or descriptors obtained through Comparative Molecular Field Analysis (CoMFA) methods. The set of molecular descriptors that is used can include any combination of the above-described types of molecular descriptors. Further, in certain example embodiments, a descriptor must satisfy various criteria in order to be used. For example, a molecular descriptor can need to be invariant to molecular numbering or labeling.

At block 306, the OPI data 102 and the molecular descriptor data 104 can be provided as input to one or more training modules 106 and computer-executable instructions of the training module(s) 106 can be executed to apply one or more training models 108 to the input data. Training the input data using the training model(s) can include determining an aggregate weight or score for each OPI with respect to each molecular descriptor based on the OPI scores/ratings provided by individuals for the molecular samples. These aggregate weights/scores can be used to generate an output model 112. The output model 112 can be, for example, a linear model with a second layer cubic correction. The output model 112 can be represented as a matrix, where each entry in the matrix is a correlation value between a particular OPI and a particular molecular descriptor. The correlation value between a particular OPI and a particular molecular descriptor can equal or can be proportional to the aggregate weight/score determined with respect to that particular OPI and molecular descriptor combination based on the execution of the training model(s) 108 on the input data. The linear output model 112 that is obtained can provide correlations between molecular descriptors and OPIs for a single individual or can be indicative of mean or median perception across an aggregate group of individuals. The training model(s) 108 can include, without limitation, an L1, L2 regression model that is applied to the OPI data 102 with respect to each of the molecular descriptors.

At block 308, prior to obtaining the output model 112, computer-executable instructions of one or more regularization module(s) 110 can be executed to cause one or more regularization algorithms to be executed on the trained input data with respect with one or more OPIs. A regularization algorithm can be executed, for example, to perform a dimensionality reduction that eliminates molecular descriptors from the output model 112 that do not have a significant impact on olfactory perception with respect to any of the OPIs or some threshold number of OPIs. A molecular descriptor can be deemed as not having a significant impact on olfactory perception (for a single individual or a group of individuals) if, for example, each respective correlation value between the molecular descriptor and each OPI fails to satisfy a correlation threshold. Depending on the implementation, a first value can satisfy a second value if the first value is greater than or equal to the second value or if the first value is less than or equal to the second value. In certain example embodiments, executing a regularization algorithm can include zeroing out entries in the output model matrix for each molecular descriptor whose correlation value with a particular OPI fails to satisfy a threshold correlation.

In certain example embodiments, an L2 multi-task learning model can be regularized with respect to an intensity OPI. Regularization with respect to intensity can include parameter tying whereby two or more OPIs are constrained across multiple individuals or predictions are constrained to be within a specified threshold from the mean perception. In certain example embodiments, a different L2 regularized output model can be learned for each individual, while at the same constraining deviation of model parameters (e.g., OPI ratings/scores) between individuals using L1 regularization. This can be interpreted as an intermediate approach between building independent models for each individual and building a model to fit the mean. However, it should be appreciated that example embodiments of the invention also include building independent output models for each individual and/or an aggregate output model that is indicative of mean perception.

At block 310, computer-executable instructions of one or more olfactory perception modules 116 can be executed to determine a set of molecular descriptors associated with a particular compound or mixture of compounds. More specifically, the olfactory perception module(s) 116 can receive new molecular descriptor data 114 that is indicative of molecular descriptors associated with a particular compound or mixture. It should be appreciated that the molecular descriptors associated with the compound or mixture can be a smaller subset of the total set of molecular descriptors that can be used to describe the chemical structure/behavior of a molecule.

At block 312, computer-executable instructions of the olfactory prediction module(s) 116 can be executed to determine, using the output model 112, a set of OPIs that are correlated with the set of molecular descriptors associated with the particular compound or mixture. The set of OPIs determined at block 312 can be, for example, those OPIs with corresponding correlation values that exceed a correlation threshold with respect to at least one molecular descriptor associated with the particular compound or mixture. The correlation values can be obtained from the output model 112. Olfactory characteristic data 118 indicative of the set of correlated OPIs can be generated and stored.

At block 314, computer-executable instructions of the olfactory prediction module(s) 116 can be executed to determine that the particular compound or mixture (or a product containing the particular compound or mixture) should be recommended to an individual based on a comparison of the correlated set of OPIs to OPI data indicative of desired or preferred OPIs of the individual. Recommendation data 120 indicative of the recommendation can be generated and stored.

In certain example embodiments, if a "pleasantness" OPI is strongly positively correlated with one or more molecular descriptors associated with the particular compound or mixture, then the compound or mixture can be recommended to an individual without evaluating specific desired/preferred OPIs associated with the individual. That is, a recommendation can be made based simply on the high degree of correlation between the "pleasantness" OPI and molecular descriptor(s) of the particular compound or mixture. An OPI can be strongly positively correlated with a molecular descriptor if, for example, a correlation value between the two satisfies a correlation threshold.

In other example embodiments, OPI data associated with an individual or a group of individuals with similar olfactory preferences can be used to target a recommendation of the compound or mixture or a product containing the compound or mixture to a particular individual. OPI data can include data indicative of historical patterns or trends in an individual's or group's responses to particular olfactory characteristics. For example, such historical data can indicate that, among some aggregate number of individuals who share similar preferences, there is a trend towards responding favorably to a particular olfactory characteristic (e.g., a sweet taste, a floral scent, etc.) or a trend towards responding negatively to some other olfactory characteristic (e.g., a bitter taste, a pungent odor, etc.). Online search data, purchase data, online browsing data, or the like can be evaluated to determine whether a group of individuals have similar preferences. OPI data associated with a particular individual can include an initial rating or survey of the consumer's preferences with respect to various odors, products, and/or environments. The user rating data for a given individual can include data indicative of how the individual has characterized olfactory attributes of various products using, for example, the example set of OPIs described earlier.

FIG. 4 is a process flow diagram of an illustrative method 400 for generating a molecular construct having desired olfactory characteristics in accordance with one or more example embodiments of the invention. FIGS. 2 and 4 will be described in conjunction with one another hereinafter.

At block 402, a set of desired OPIs can be identified. The set of desired OPIs can be associated with a particular individual or a group of individuals. The set of desired OPIs can include, for example, the "pleasantness" OPI and/or any OPI that is strongly correlated with the "pleasantness" OPI. For example, those OPI(s) having high positive correlation values for a threshold number of same molecular descriptors as the "pleasantness" OPI can be selected.

At block 404, computer-executable instructions of one or more model inversion module(s) 204 can be executed to invert an output model 202 to obtain an inverted output model 206. The output model 202 can be the output model 112 generated in accordance with the method 300 of FIG. 3. If, for example, the output model 202 is represented as matrix of correlation values, the inverted model 206 can be the inverse matrix of the output model matrix. The inverse matrix can be a matrix that when multiplied by the output model matrix yields the identity matrix. Linearity of the output model 202 can allow for it to be inverted.

At block 406, computer-executable instructions of one or more molecular construct determination modules 210 can be executed to determine, using the inverted output model 206, a set of molecular descriptors that are correlated with the set of desired OPIs. Data 208 indicative of the determined set of molecular descriptors can be generated and stored. In particular, if the inverted output model 206 is represented as a matrix (e.g., an inverse matrix of the output model matrix), entries in the inverted output model matrix can be evaluated to determine the set of molecular descriptors that are strongly correlated with the set of desired OPIs.

At block 408, the molecular descriptor data 208 can be provided as input to the molecular construct determination module(s) 210, and computer-executable instructions of the module(s) 210 can be executed to determine whether it is feasible to generate a molecular construct that satisfies the set of molecular descriptors. The molecular construct determination module(s) 210 can utilize other types of data (e.g., chemical compound data) to determine the feasibility of the molecular construct. For example, the set of molecular descriptors can include a particular set of elements, a particular set of chemical bonds, or the like that cannot be structurally arrange in a manner that would satisfy all of the set of molecular descriptors. In such a scenario, a negative determination would be made at block 408, and the method 400 ends. On the other hand, if the molecular construct is feasible, a positive determination is made at block 408, and the method 400 proceeds to block 410 where the molecular construct is generated based on the set of molecular descriptors.

Example embodiments of the invention provide various technical features, technical effects, and/or improvements to technology. For instance, example embodiments of the invention provide the technical effect of predicting olfactory perception for a single individual or across a group of individuals based molecular structure. This technical effect is achieved by at least in part by the technical feature of generating a linear output model that specifies correlations between OPIs and molecular descriptors that can be determined based on user ratings of molecular samples across different OPIs. Example embodiments of the invention also provide the technical effect of generating a molecular construct having desired olfactory properties. This technical effect is achieved at least in part by the technical feature of providing a linear output model that is invertible. The above-described technical effects constitute an improvement to the functioning of a computer configured to predict olfactory perception of chemical compounds and mixtures. In addition, the above-described technical effects constitute an improvement to any of a variety of technological fields including any of those previously described such as, for example, appetite management, odor cancellation, or the like. It should be appreciated that the above examples of technical features, technical effects, improvements to the functioning of a computer, and improvements to technological fields provided by example embodiments of the invention are merely illustrative and not exhaustive.

One or more illustrative embodiments of the invention are described herein. Such embodiments are merely illustrative of the scope of this invention and are not intended to be limiting in any way. Accordingly, variations, modifications, and equivalents of embodiments described herein are also within the scope of the invention.

Figure 5:
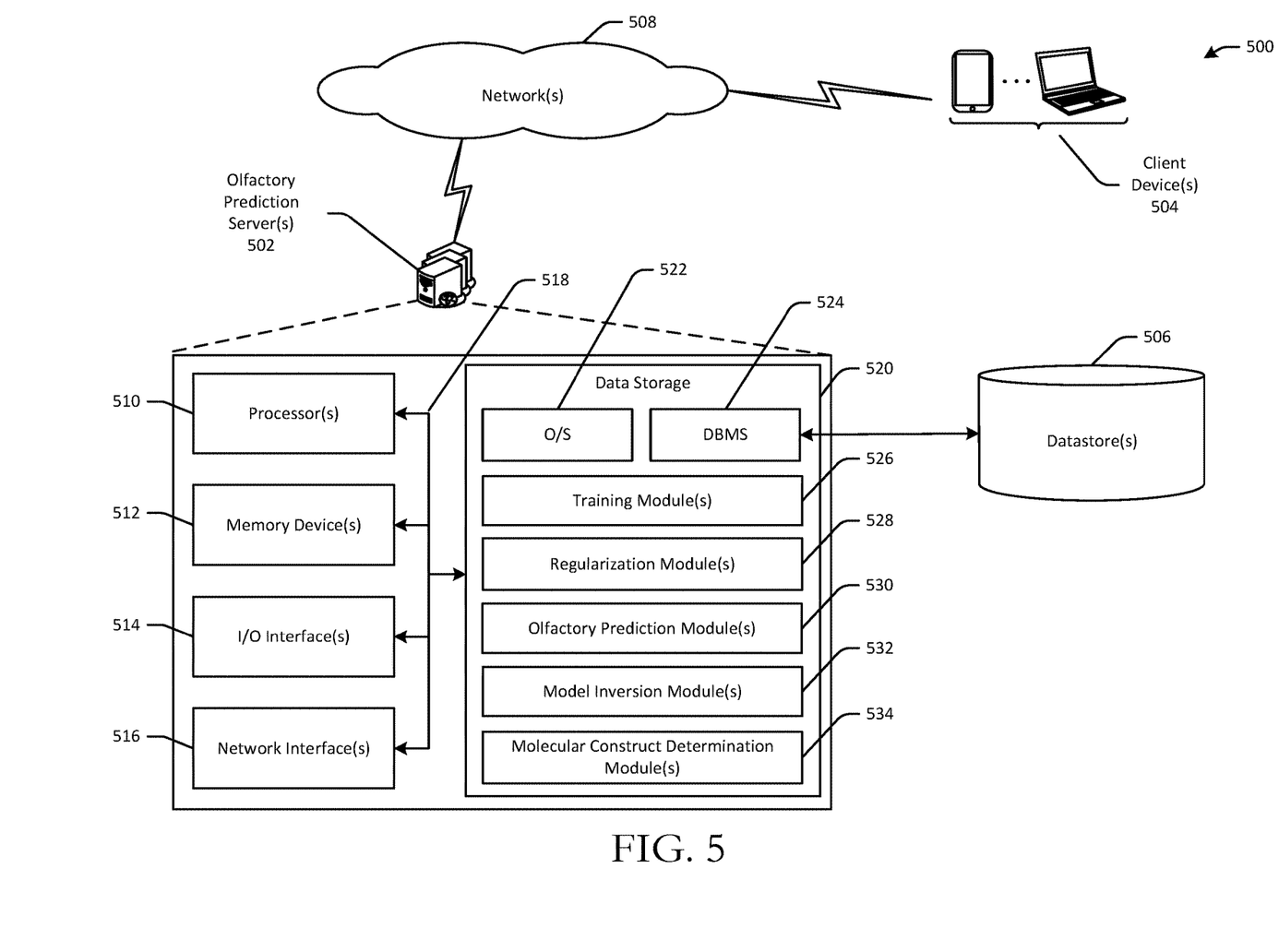
FIG. 5 is a schematic diagram of an illustrative networked architecture in accordance with one or more example embodiments of the invention.

FIG. 5 is a schematic diagram of an illustrative networked architecture 500 in accordance with one or more example embodiments of the invention. The networked architecture can include one or more olfactory prediction servers 502 that are configured to communicate with one or more client devices 504 over one or more networks 508. While one or more components of the networked architecture 500 are described herein in the singular at times, it should be appreciated that multiple instances of any such component can be provided, and functionality described in connection with a particular component can instead be distributed across such multiple instances.

The client device(s) 504 can include, without limitation, a smartphone, a tablet, a wearable device, a personal computer, or any other suitable user device. The network(s) 508 can include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. The network(s) 508 can have any suitable communication range associated therewith and can include, for example, global networks (e.g., the Internet), metropolitan area networks (MANs), wide area networks (WANs), local area networks (LANs), or personal area networks (PANs). In addition, the network(s) 508 can include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the olfactory prediction server 502 can include one or more processors (processor(s)) 510, one or more memory devices 512 (generically referred to herein as memory 512), one or more input/output ("I/O")

interface(s) 514, one or more network interfaces 516, and data storage 520. The olfactory prediction server 502 can further include one or more buses 518 that functionally couple various components of the olfactory prediction server 502.

The bus(es) 518 can include at least one of a system bus, a memory bus, an address bus, or a message bus, and can permit the exchange of information (e.g., data (including computer-executable code), signaling, etc.) between various components of the olfactory prediction server 502. The bus(es) 518 can include, without limitation, a memory bus or a memory controller, a peripheral bus, an accelerated graphics port, and so forth. The bus(es) 518 can be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 512 can include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, can include non-volatile memory. In certain example embodiments, volatile memory can enable faster read/write access than non-volatile memory. However, in certain other example embodiments, certain types of non-volatile memory (e.g., FRAM) can enable faster read/write access than certain types of volatile memory.

In various implementations, the memory 512 can include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 512 can include main memory as well as various forms of cache memory such as instruction cache(s), data cache(s), translation lookaside buffer(s) (TLBs), and so forth. Further, cache memory such as a data cache can be a multi-level cache organized as a hierarchy of one or more cache levels (L1, L2, etc.).

The data storage 520 can include removable storage and/or non-removable storage including, but not limited to, magnetic storage, optical disk storage, and/or tape storage. The data storage 520 can provide non-volatile storage of computer-executable instructions and other data. The memory 512 and the data storage 520, removable and/or non-removable, are examples of computer-readable storage media (CRSM) as that term is used herein.

The data storage 520 can store computer-executable code, instructions, or the like that can be loadable into the memory 512 and executable by the processor(s) 510 to cause the processor(s) 510 to perform or initiate various operations. The data storage 520 can additionally store data that can be copied to memory 512 for use by the processor(s) 510 during the execution of the computer-executable instructions. Moreover, output data generated as a result of execution of the computer-executable instructions by the processor(s) 510 can be stored initially in memory 512 and can ultimately be copied to data storage 520 for non-volatile storage.

More specifically, the data storage 520 can store one or more operating systems (O/S) 522; one or more database management systems (DBMS) 524 configured to access the memory 512 and/or one or more external datastore(s) 506; and one or more program modules, applications, engines, computer-executable code, scripts, or the like such as, for example, one or more training modules 526, one or more regularization modules 528, one or more olfactory prediction modules 530, one or more model inversion modules 532, and one or more molecular construct determination modules 534. Any of the components depicted as being stored in data storage 520 can include any combination of software, firmware, and/or hardware. The software and/or firmware can include computer-executable instructions (e.g., computer-executable program code) that can be loaded into the memory 512 for execution by one or more of the processor(s) 510 to perform any of the operations described earlier in connection with correspondingly named modules. In certain example embodiments, the client device(s) 504 can be configured to communicate with the olfactory prediction server 502 to send data (e.g., OPI data) to the olfactory prediction server 502 and/or obtain results of processing performed by the depicted program modules. In other example embodiments, one or more of the depicted program modules can reside, at least partially, on a client device 504 as part of a client application executable on the client device 504, for example.

Although not depicted in FIG. 5, the data storage 520 can further store various types of data utilized by components of the olfactory prediction server 402 (e.g., any of the types of data depicted in and described with respect to FIG. 1 or FIG. 2). Any data stored in the data storage 520 can be loaded into the memory 512 for use by the processor(s) 510 in executing computer-executable instructions. In addition, any data stored in the data storage 520 can potentially be stored in the datastore(s) 506 and can be accessed via the DBMS 524 and loaded in the memory 512 for use by the processor(s) 510 in executing computer-executable instructions.

The processor(s) 510 can be configured to access the memory 512 and execute computer-executable instructions loaded therein. For example, the processor(s) 510 can be configured to execute computer-executable instructions of the various program modules, applications, engines, or the like of the olfactory prediction server 502 to cause or facilitate various operations to be performed in accordance with one or more embodiments of the invention. The processor(s) 510 can include any suitable processing unit capable of accepting data as input, processing the input data in accordance with stored computer-executable instructions, and generating output data. The processor(s) 510 can include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 510 can have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 510 can be capable of supporting any of a variety of instruction sets.

Referring now to other illustrative components depicted as being stored in the data storage 520, the O/S 522 can be loaded from the data storage 520 into the memory 512 and can provide an interface between other application software executing on the olfactory prediction server 502 and hardware resources of the olfactory prediction server 502. More specifically, the O/S 522 can include a set of computer-executable instructions for managing hardware resources of the olfactory prediction server 502 and for providing common services to other application programs. In certain example embodiments, the O/S 522 can include or otherwise control execution of one or more of the program modules depicted as being stored in the data storage 520. The O/S 522 can include any operating system now known or which can be developed in the future including, but not limited to, any server operating system, any mainframe operating system, or any other proprietary or non-proprietary operating system.

The DBMS 524 can be loaded into the memory 512 and can support functionality for accessing, retrieving, storing, and/or manipulating data stored in the memory 512, data stored in the data storage 520, and/or data stored in the datastore(s) 506. The DBMS 524 can use any of a variety of database models (e.g., relational model, object model, etc.) and can support any of a variety of query languages. The DBMS 524 can access data represented in one or more data schemas and stored in any suitable data repository. The datastore(s) 506 can include, but are not limited to, databases (e.g., relational, object-oriented, etc.), file systems, flat files, distributed datastores in which data is stored on more than one node of a computer network, peer-to-peer network datastores, or the like.

Referring now to other illustrative components of the olfactory prediction server 502, the input/output (I/O) interface(s) 514 can facilitate the receipt of input information by the olfactory prediction server 502 from one or more I/O devices as well as the output of information from the olfactory prediction server 502 to the one or more I/O devices. The I/O devices can include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components can be integrated into the olfactory prediction server 502 or can be separate. The I/O devices can further include, for example, any number of peripheral devices such as data storage devices, printing devices, and so forth.

The I/O interface(s) 514 can also include an interface for an external peripheral device connection such as universal serial bus (USB), FireWire, Thunderbolt, Ethernet port or other connection protocol that can connect to one or more networks. The I/O interface(s) 514 can also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The olfactory prediction server 502 can further include one or more network interfaces 516 via which the olfactory prediction server 502 can communicate with any of a variety of other systems, platforms, networks, devices, and so forth. The network interface(s) 516 can enable communication, for example, with one or more client devices 504 via one or more of the network(s) 508.

It should be appreciated that the engines depicted in FIG. 5 as being stored in the data storage 520 are merely illustrative and not exhaustive and that processing described as being supported by any particular program module can alternatively be distributed across multiple modules, engines, or the like, or performed by a different module, engine, or the like. In addition, various program module(s), script(s), plug-in(s), Application Programming Interface(s) (API(s)), or any other suitable computer-executable code hosted locally on the olfactory prediction server 502 and/or hosted on other computing device(s) accessible via one or more of the network(s) 508, can be provided to support functionality provided by the program modules depicted in FIG. 5 and/or additional or alternate functionality. Further, functionality can be modularized in any suitable manner such that processing described as being performed by a particular program module can be performed by a collection of any number of engines or program modules, or functionality described as being supported by any particular program module can be supported, at least in part, by another program module. In addition, program modules that support the functionality described herein can be executable across any number of devices 502 in accordance with any suitable computing model such as, for example, a client-server model, a peer-to-peer model, and so forth. In addition, any of the functionality described as being supported by any of the program modules depicted in FIG. 5 can be implemented, at least partially, in hardware and/or firmware across any number of devices.

It should further be appreciated that the olfactory prediction server 502 can include alternate and/or additional hardware, software, or firmware components beyond those described or depicted without departing from the scope of the invention. More particularly, it should be appreciated that software, firmware, or hardware components depicted as forming part of the olfactory prediction server 502 are merely illustrative and that some components can be absent or additional components can be provided in various embodiments. While various illustrative program modules have been depicted and described as software modules stored in data storage 520, it should be appreciated that functionality described as being supported by the program modules can be enabled by any combination of hardware, software, and/or firmware. It should further be appreciated that each of the above-mentioned program modules represents, in various embodiments, a logical partitioning of supported functionality. This logical partitioning is depicted for ease of explanation of the functionality and is not necessarily representative of the structure of software, hardware, and/or firmware for implementing the functionality. Accordingly, it should be appreciated that functionality described as being provided by a particular program module can, in various embodiments, be provided at least in part by one or more other program modules. Further, one or more depicted program modules can be absent in certain embodiments, while in other embodiments, additional program modules and/or engines not depicted can be present and can support at least a portion of the described functionality and/or additional functionality.

One or more operations of the method 300 or the method 400 can be performed by an olfactory prediction server 502 having the illustrative configuration depicted in FIG. 5, or more specifically, by one or more program modules, engines, applications, or the like executable on such a device. It should be appreciated, however, that such operations can be implemented in connection with numerous other device configurations.

The operations described and depicted in the illustrative method 300 of FIG. 3 or the illustrative method 400 of FIG.

4 can be carried out or performed in any suitable order as desired in various example embodiments of the invention. Additionally, in certain example embodiments, at least a portion of the operations can be carried out in parallel. Furthermore, in certain example embodiments, less, more, or different operations than those depicted in FIG. 3 or FIG. 4 can be performed.

Although specific embodiments of the invention have been described, one of ordinary skill in the art will recognize that numerous other modifications and alternative embodiments are within the scope of the invention. For example, any of the functionality and/or processing capabilities described with respect to a particular system, system component, device, or device component can be performed by any other system, device, or component. Further, while various illustrative implementations and architectures have been described in accordance with embodiments of the invention, one of ordinary skill in the art will appreciate that numerous other modifications to the illustrative implementations and architectures described herein are also within the scope of this invention. In addition, it should be appreciated that any operation, element, component, data, or the like described herein as being based on another operation, element, component, data, or the like can be additionally based on one or more other operations, elements, components, data, or the like. Accordingly, the phrase "based on," or variants thereof, should be interpreted as "based at least in part on."

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for correlating molecular structure with olfactory perception, the method comprising:
   obtaining training olfactory perception indicator (OPI) data for a group of molecular samples, the training OPI data comprising values of a set of OPIs for each of the molecular samples;
   obtaining molecular descriptor data associated with the group of molecular samples;
   executing one or more training models on input data to obtain an output model, the input data comprising the training OPI data and the molecular descriptor data, the output model specifying correlations between a set of molecular descriptors described by the molecular descriptor data and the set of OPIs;
   obtaining target OPIs associated with an individual;
   inverting the output model to obtain an inverted output model;
   determining, using the inverted output model, a subset of the set of molecular descriptors that are correlated to the target OPIs; and
   generating a molecular construct that satisfies the subset of the set of molecular descriptors.

2. The computer-implemented method of claim 1, further comprising:
   generating trained input data by executing the one or more training models on the input data; and
   executing one or more regularization algorithms on the trained input data with respect to one or more OPIs in the set of OPIs to obtain the output model.

3. The computer-implemented method of claim 1, wherein obtaining the training OPI data comprises receiving the values of the set of OPIs for each of the molecular samples from an aggregate group of individuals.

4. The computer-implemented method of claim 1, wherein obtaining the training OPI data comprises receiving the values of the set of OPIs for each of the molecular samples from a single individual.

5. The computer-implemented method of claim 1, wherein determining the subset of the set of OPIs that is correlated with the subset of the set of molecular descriptors comprises determining that the subset of the set of OPIs is positively correlated with the subset of the set of molecular descriptors.

6. The computer-implemented method of claim 5, wherein determining the subset of the set of OPIs that is correlated with the subset of the set of molecular descriptors further comprises determining that each respective correlation between an OPI in the subset of the set of OPIs and a corresponding molecular descriptor in the subset of the set of molecular descriptors satisfies a threshold value.

7. The computer-implemented method of claim 1, wherein the output model is a linear model.

8. The computer-implemented method of claim 1, further comprising predicting an olfactory response of an individual to the particular chemical compound or mixture based at least in part on an amount of overlap between the subset of the set of OPIs that is correlated with the subset of the set of molecular descriptors and a set of desired OPIs associated with the individual.

9. The computer-implemented method of claim 1, wherein the output model is a linear model.

10. The computer-implemented method of claim 1, wherein the at least one processor is further configured to execute the computer-executable instructions to predict an olfactory response of an individual to the particular chemical compound or mixture based at least in part on an amount of overlap between the subset of the set of OPIs that is correlated with the subset of the set of molecular descriptors and a set of desired OPIs associated with the individual.

11. A system for correlating molecular structure with olfactory perception, the system comprising:
    at least one memory storing computer-executable instructions; and
    at least one processor configured to access the at least one memory and execute the computer-executable instructions to:
      obtain training olfactory perception indicator (OPI) data for a group of molecular samples, the training OPI data comprising values of a set of OPIs for each of the molecular samples;
      obtain molecular descriptor data associated with the group of molecular samples;
      execute one or more training models on input data to obtain an output model, the input data comprising the training OPI data and the molecular descriptor data, the output model specifying correlations between a set of molecular descriptors described by the molecular descriptor data and the set of OPIs;
      obtain target OPIs associated with an individual;
      invert the output model to obtain an inverted output model;
      determine, using the inverted output model, a subset of the set of molecular descriptors that are correlated to the target OPIs; and
      generate a molecular construct that satisfies the subset of the set of molecular descriptors.

12. The system of claim 11, wherein the at least one processor is further configured to execute the computer-executable instructions to:
    generate trained input data by executing the one or more training models on the input data; and
    execute one or more regularization algorithms on the trained input data with respect to one or more OPIs in the set of OPIs to obtain the output model.

13. The system of claim 11, wherein the at least one processor is configured to obtain the training OPI data by executing the computer-executable instructions to receive the values of the set of OPIs for each of the molecular samples from an aggregate group of individuals.

14. The system of claim 11, wherein the at least one processor is configured to obtain the training OPI data by executing the computer-executable instructions to receive the values of the set of OPIs for each of the molecular samples from a single individual.

15. The system of claim 11, wherein the at least one processor is configured to determine the subset of the set of OPIs that is correlated with the subset of the set of molecular descriptors by executing the computer-executable instructions to determine that the subset of the set of OPIs is positively correlated with the subset of the set of molecular descriptors.

16. The system of claim 15, wherein the at least one processor is configured to determine the subset of the set of OPIs that is correlated with the subset of the set of molecular descriptors by executing the computer-executable instructions to determine that each respective correlation between an OPI in the subset of the set of OPIs and a corresponding molecular descriptor in the subset of the set of molecular descriptors satisfies a threshold value.

17. A computer program product for generating a molecular construct based at least in part on a correlation with olfactory perception, the computer program product comprising a non-transitory storage medium readable by a processing circuit, the storage medium storing instructions executable by the processing circuit to cause a method to be performed, the method comprising:
   identifying a set of desired olfactory prediction indicators (OPIs);
   inverting an output model to obtain an inverted output model;
   determining, using the inverted output model, a set of molecular descriptors that are correlated with the set of desired OPIs;
   determining that generation of the molecular construct based at least in part on the set of molecular descriptors is feasible; and
   generating the molecular construct.

18. The computer program product of claim 17, the method further comprising:
   identifying a consumer associated with the set of desired OPIs; and
   recommending a product containing the molecular construct to the consumer.

19. The computer program product of claim 17, wherein the set of molecular descriptors is a first set of molecular descriptors, and wherein the output model is a matrix that comprises correlations between a set of OPIs and a second set of molecular descriptors, the set of OPIs comprising the set of desired OPIs and the second set of molecular descriptors comprising the first set of molecular descriptors.

20. The computer program product of claim 19, wherein the correlations are determined based at least in part on intensity values of the set of OPIs specified by one or more individuals with respect to a set of molecular samples comprising at least a portion of the second set of molecular descriptors.

* * * * *

UNITED STATES PATENT AND TRADEMARK OFFICE
CERTIFICATE OF CORRECTION

PATENT NO. : 10,665,330 B2  
APPLICATION NO. : 15/296597  
DATED : May 26, 2020  
INVENTOR(S) : Cecchi et al.

Page 1 of 1

It is certified that error appears in the above-identified patent and that said Letters Patent is hereby corrected as shown below:

On the Title Page

Item (72) Inventors: should read as follows:  
...Guillermo A. Cecchi, New York, NY (US);  
Amit Dhurandhar, Yorktown Heights, NY (US);  
Pablo Meyer Rojas, Yorktown Heights, NY (US)

Signed and Sealed this  
Eighteenth Day of August, 2020

Andrei Iancu  
*Director of the United States Patent and Trademark Office*